United States Patent [19]
Richelsoph

[11] Patent Number: 5,342,363
[45] Date of Patent: Aug. 30, 1994

[54] MEDICAL INSTRUMENT AND PROCEDURE

[75] Inventor: Marc E. Richelsoph, Cordova, Tenn.

[73] Assignee: Wright Medical Technology, Inc., Arlington, Tenn.

[21] Appl. No.: 984,066

[22] Filed: Nov. 30, 1992

[51] Int. Cl.$^5$ .......................... A61F 2/54; A61B 19/00
[52] U.S. Cl. .......................... 606/79; 606/80; 606/86; 606/89; 606/96; 606/98; 623/66; 128/898
[58] Field of Search .......................... 606/79, 80, 82, 85, 606/86, 87, 89, 96, 98; 623/16, 18, 22, 23, 66; 128/897, 898

[56] References Cited

U.S. PATENT DOCUMENTS

| | | | |
|---|---|---|---|
| 4,187,559 | 2/1980 | Grell et al. | 623/18 |
| 4,738,256 | 4/1988 | Freeman et al. | 606/87 X |
| 4,790,852 | 12/1988 | Noiles | 623/18 |
| 5,047,034 | 9/1991 | Sohngen | 606/96 X |
| 5,135,529 | 8/1992 | Paxson et al. | 606/85 |
| 5,171,245 | 12/1992 | Cezana | 606/86 |
| 5,190,547 | 3/1993 | Barber, Jr. et al. | 606/79 |

FOREIGN PATENT DOCUMENTS 3538654 4/1987 Fed. Rep. of Germany ........ 606/80

OTHER PUBLICATIONS

Translation of German Patent DT 3538654.

Primary Examiner—Randall L. Green
Assistant Examiner—Dinh X. Nguyen
Attorney, Agent, or Firm—Walker, McKenzie & Walker

[57] ABSTRACT

A medical instrument and procedure mills a groove at a precise angle and location in a partially formed bone canal that has been drilled and reamed to provide a frustoconical seat for a prosthesis stem that has a conical proximal region. The groove finishes preparation of the canal in a precise manner so that an anti-rotation lug attached to the conical proximal region of the prosthesis stem seats in the finished canal accurately.

14 Claims, 4 Drawing Sheets

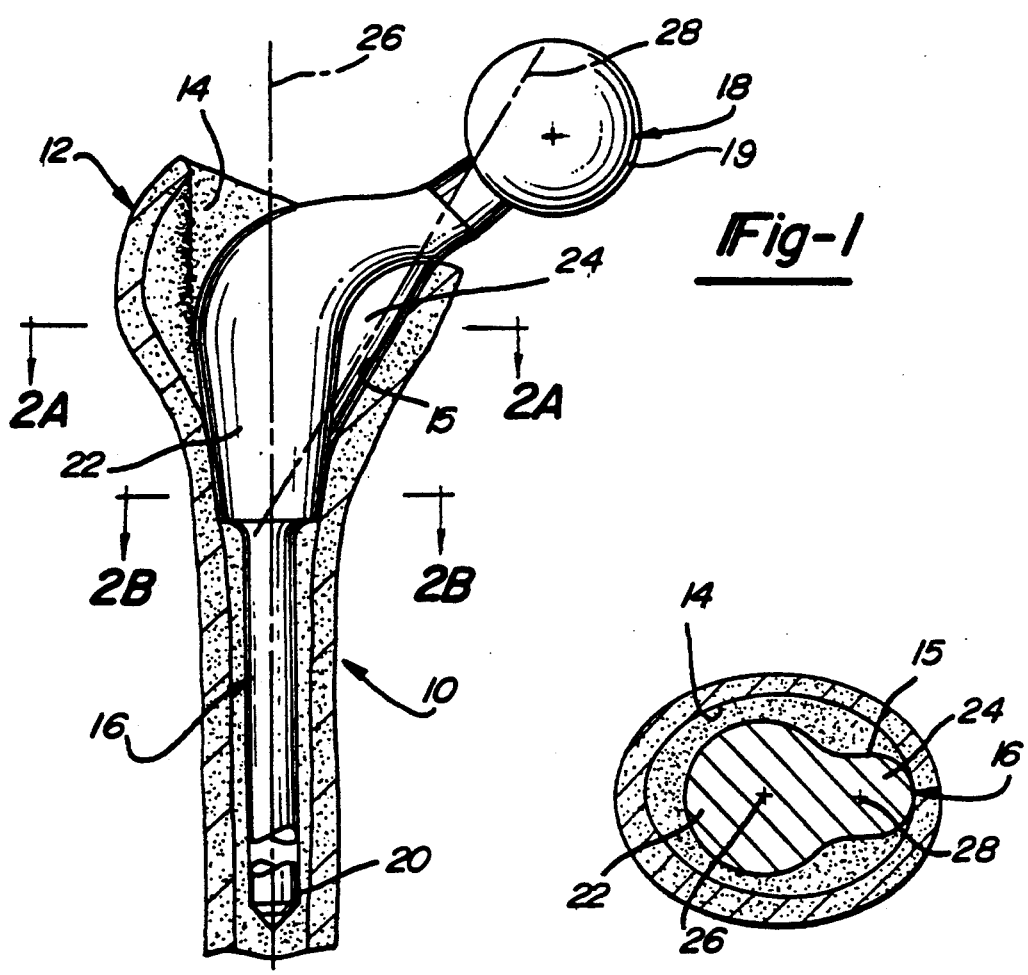
Fig-1
Fig-2A
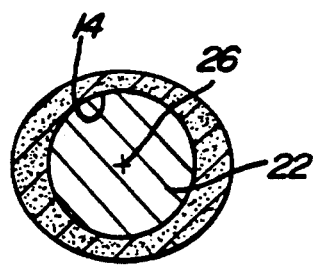
Fig-2B
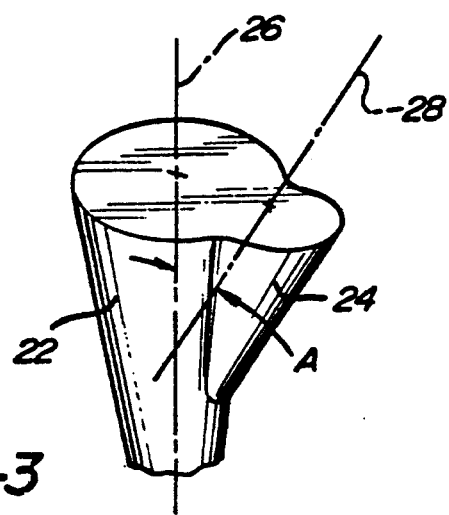
Fig-3

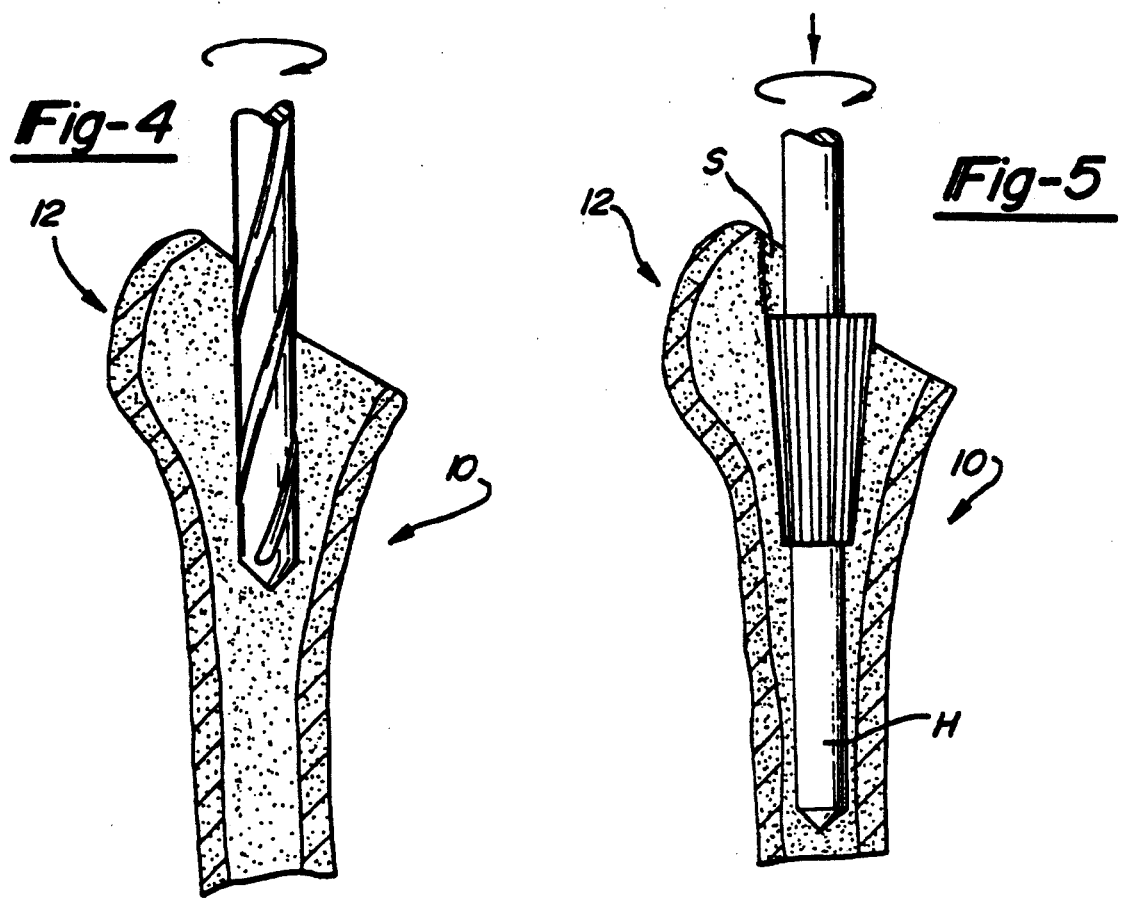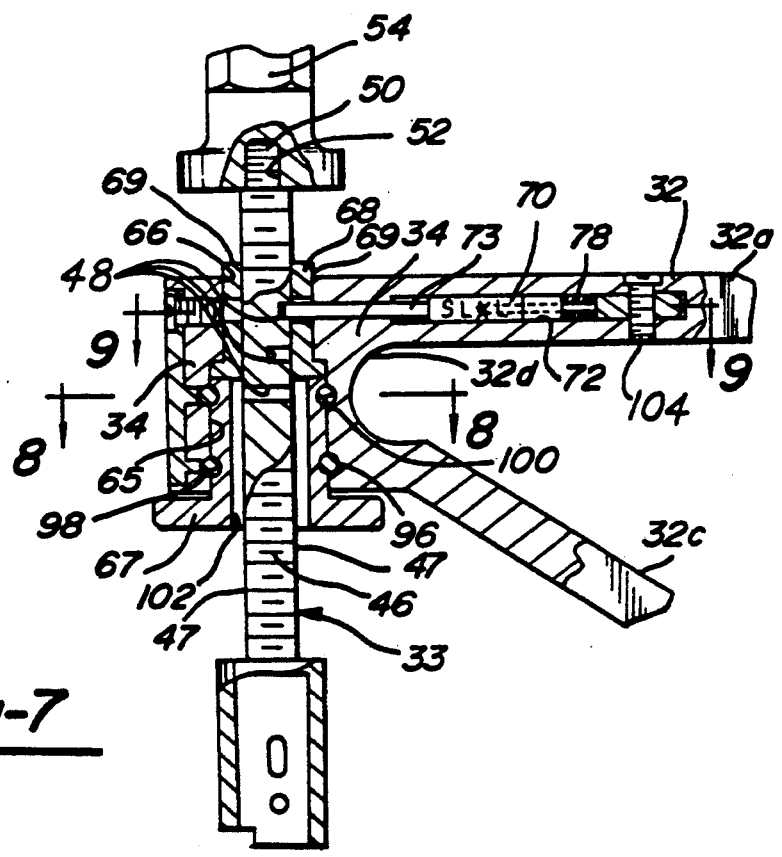

MEDICAL INSTRUMENT AND PROCEDURE

TECHNICAL FIELD

This invention relates to medical instruments and procedures and more particularly to a medical instrument and procedure for the accurate preparation of a bone canal for good cortical contact with and proper load transfer from the stem of a prosthesis.

BACKGROUND OF THE INVENTION

In the development of advanced press-fit prosthesis stems, such as hip stems, accurate preparation of the bone canal is extremely important in order to guarantee good cortical contact with and load transfer from the stem to the bone. Examples of prior art press-fit prosthetic hip stems may be had in the Dow Corning Wright publication "McCutchen Hip System" bearing copyright date 1988 and identification number 235-1187T. Some existing prosthesis stems are designed with a conical proximal region to distribute the load and an anti-rotation lug to fix and maintain the accurate position of the joint portion of the prosthesis.

Bone canals for these prosthesis stems are presently prepared by drilling the resected distal end of the bone and then reaming the drilled hole to provide a frustoconical seat for the trochanteral portion of the prosthesis stem. The bone canal is then cut at an angle with a milling cutter to provide a slanted groove for seating the anti-rotation lug by dead-reckoning, i.e., by the surgeon eyeballing the appropriate location of the tool axis and angle in a procedure that often does not result in accurate seating of the anti-rotation lug. Alternatively, the bone canal can be prepared as taught in U.S. Pat. No. 5,135,529 to Paxson et al, issued Aug. 4, 1992 and assigned to the assignee of the subject invention, the disclosure of which is hereby incorporated by reference and relied upon. In Paxson et al, modular unitary rasp blocks of varying sizes are used to form the slanted groove to receive the anti-rotation lug. Again, the procedure often does not result in accurate seating of the anti-rotation lug.

The primary disadvantage of the prior art bone canal preparation techniques is that accurate and predictable results are difficult to obtain. Additionally, the prior art medical instruments used to prepare the bone canal for prosthesis implantation are often cumbersome and somewhat difficult for a single surgeon to operate, and often do not readily adapt themselves for accommodating various prosthesis stem configurations.

SUMMARY OF THE INVENTION

The invention contemplates a medical instrument for preparing the proximal end of a femur to receive a prosthesis having an attached anti-rotation lug. The medical instrument comprises a frame having two spaced frame portions. A post is attached to one of the frame portions and defines a reference axis. A tool guide is attached to the other of the frame portions and defines a tool axis which is fixed at a precise angle with respect to the reference axis. A fixture means extends from the post for attaching to a frustoconical seat in a partially prepared canal in the femur to locate the reference axis in relation to the prepared canal so that the tool guide and the tool axis are set at the precise angle for guiding a rotary cutting tool in the partially prepared canal to accommodate the anti-rotation lug of the prosthesis when implanted in the femur.

The subject invention overcomes the disadvantages inherent in the prior art by the instrument including fixture means which temporarily mates with, or seats in, the formed frustoconical seat in the femur to accurately, precisely and predictly locate the tool axis of the tool guide so that a portion of the femur can be resected to accommodate the anti-rotation lug of the prosthesis. By seating in the prepared frustoconical seat in the proximal end of the femur, the subject medical instrument is operated during surgical implantation with less difficulty, more versatility, and more accuracy than heretofore possible.

BRIEF DESCRIPTION OF THE DRAWINGS

The above and other objects, features and advantages of the invention will become more apparent from the following description taken in conjunction with the accompanying drawings wherein like references refer to like parts and wherein:

FIG. 1 is a cross section of a resected femur having a prosthesis fitted into the intramedullary canal of the proximal end of the femur which has been shaped using the medical instrument and procedure of this invention;

FIGS. 2a and 2b are sections respectively taken substantially along the lines 2a—2a and 2b—2b of FIG. 1 perpendicular to the longitudinal axis of the stem;

FIG. 3 is a fragmentary perspective view of the trochanteral portion showing the anti-rotation lug of the prosthesis depicted in FIGS. 1 and 2a and 2b;

FIGS. 4, 5 and 6 are each cross-sectional views of the resected femur of FIG. 1 showing various stages of preparing the canal for the prosthesis with FIG. 6 illustrating the medical instrument of this invention in place for a rotary cutting procedure further in accordance with this invention;

FIG. 7 is a partially sectioned and fragmentary enlargement of the medical instrument;

DESCRIPTION OF THE INVENTION

Figure 6:
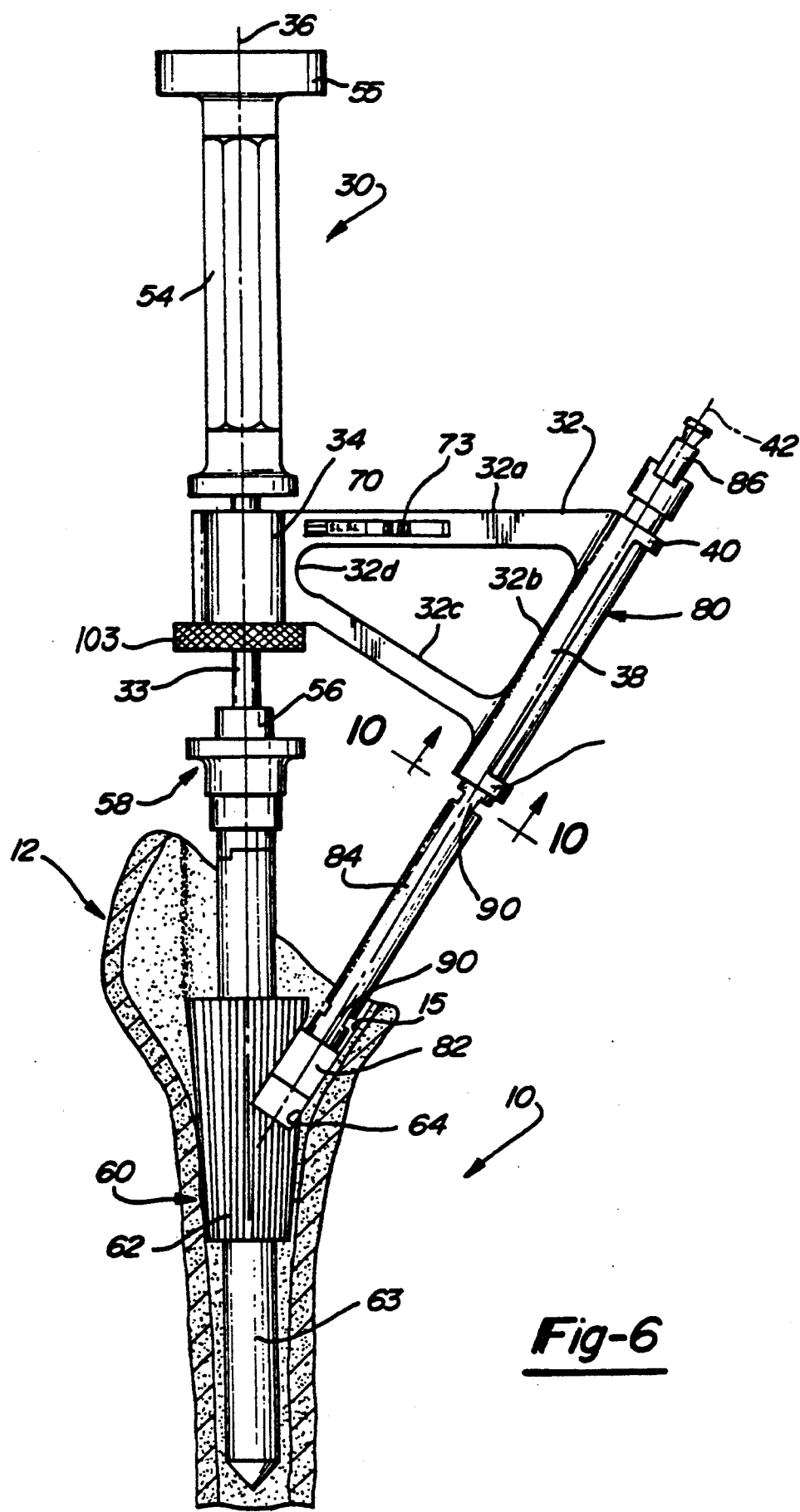

Referring now to the drawings and by way of background, FIGS. 1, 2a, 2b and 3, show a femur 10 having a resected proximal end 12. The inner aspect of the end 12 has been drilled, reamed and milled to form a canal 14 for receiving the stem 16 of a proximal femoral prosthesis 18 bearing the ball member 19 of a total implantable hip joint. The distal portion of the stem 16 is formed with a rounded tip 20 while the proximal portion has a bulbous shape that includes a conically shaped trochanteral portion 22 and a longitudinally extending lug 24 integral with the trachanteral portion 22. The tip 20 and the trochanteral portion 22 are coaxially aligned on a longitudinal axis 26 extending throughout the imaginary centerline of the medullary canal of the femur 10. The lug 24 is slanted with respect to the axis 26 and intersects the trochanteral portion 22. The lug 24, which keeps the prosthesis 18 from rotating in the canal 14, is formed from the protruding portion of a straight cylindrical body of revolution about a slanted axis 28 that intersects the axis 26 at a precise slant angle A, as best shown in FIGS. 1 and 3. Thus the canal 14 requires a slanted, partially cylindrical groove 15 for the lug 24. The groove 15 describes a bi-lobal cross section proximally, as shown in FIG. 2a, and a circular cross section distally, as shown in FIG. 2b.

A preferred surgical procedure for preparing the canal 14 is shown in FIGS. 4, 5 and 6. First, the resected proximal end 12 of the femur 10 is drilled as shown in FIG. 4 to provide a blind hole H displacing the cancellous bone, of proper size and depth for the tip 20. The proximal end of the hole H is then countersunk with a frustoconical reamer to form a frustoconical seat S that is the proper size and shape for the trochanteral portion 22, as shown in FIG. 5. The size of the frustoconical reamer and the depth of the countersink is preferably such that the periphery of the frustoconical seat S exposes cortical bone. The hole H and frustoconical seat S are precisely cut on the same axis 26, i.e., the hole H and seat S are coaxial. These procedures are basic to preparing the canal 14 and represent standard, well-known techniques. However, an additional procedure is still needed to complete the canal 14 for accommodating the anti-rotation lug 24, which additional procedure is set forth below.

In combination with the above, this invention is further concerned with a medical instrument and procedure for cutting the slanted groove 15 in the partially prepared wall of the canal 14 in a precise and accurate manner so that the anti-rotation lug 24 snugly seats in the groove 15 of the finished canal 14.

The medical instrument of this invention is shown generally at 30 in FIGS. 6 through 11, with FIG. 6 illustrating the instrument in place while the groove 15 is being cut to finally prepare the canal 14 for accurate fitting of the stem 16 particularly the trochanteral portion 22 with the integral anti-rotation lug 24.

Figure 8:
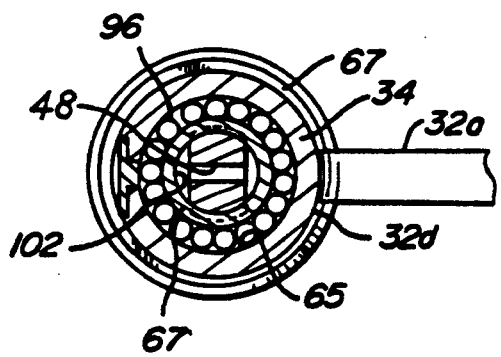
FIG. 8 is a section taken substantially along the line 8—8 of FIG. 7.
Figure 9:
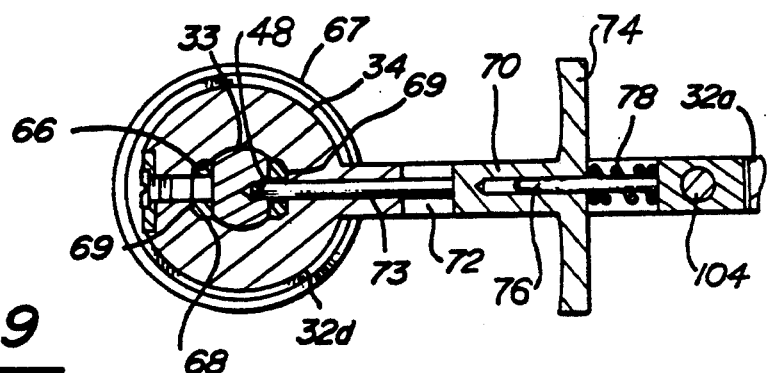
FIG. 9 is a section taken substantially along the line 9—9 of FIG. 7.
Figure 10:
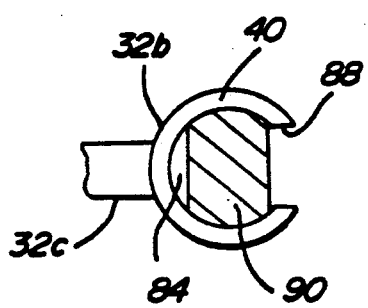
FIG. 10 is a section taken substantially along the line 10—10 of FIG. 6.

The medical instrument 30 preferably comprises a quadrilateral frame 32 having four non-parallel sides 32a, 32b, 32c, 32d respectively spaced apart from one another. A post 33 is attached to one of the non-parallel sides 32d by a coaxial collar 34 that forms an integral part of the frame 32. The post 33 and collar 34 establish and define a reference axis 36 for the frame 32 which is substantially coincidental with the axis 26 of the prosthesis stem 16 to be implanted in the canal 14. As shown in FIGS. 8 and 9, the bore of the collar 34 has a distal circular portion 65 and a proximal keyway 66 smaller than the circular portion 65.

The other non-parallel side 32b of the frame 32, opposite the collar 34, has an integral tool guide 38 comprising two axially spaced collars 40 which define a tool or cutting axis 42. The tool axis 42 is fixed at a precise slant angle A with respect to the reference axis 36 so that the tool axis 42 substantially coincides with the axis 28 of the anti-rotation lug 24 when the reference axis 36 is superimposed on the axis 26 of the trochanteral portion 22. Thus, the collars 40 guide a cutting head 82 along the tool axis 42 to resect a groove 15 in the proximal femur 16 precisely angularly positioned to receive the lug 24 of the stem 16 during implantation.

The post 33 comprises a threaded shank 46 having diametrically-opposed flats 47 and a series of three cross bores 48 which can be varied in number. The proximal end of the post 33 comprises a threaded shank 50, of smaller diameter than the shank 46, that also has flats 52 and a cross bore (not shown). A coaxial handle 54 is screwed onto the smaller shank 50 at the top, or proximal end of the post 33 and retained by a pin inserted through the cross bore (not shown). The handle 54 has an enlarged, flat proximal thumb pad 55.

The distal end of the post 33 has a collet 56 forming part of a quick-disconnect coupling 58 used to attach the medical instrument 30 to a fixture 60. The fixture 60 comprises a frustoconical portion 62 and pin 63 that match the size and shape of the trochanteral portion 22 and tip 20 of the stem 16. In this embodiment, depicted in FIG. 6, the cone 62 does not include an anti-rotation lug. However, it has a slanted bore 64 that intersects its peripheral surface. The axes of the bore 64 and the fixture frustoconical portion 62 form an angle that duplicates the slant angle A formed by the axis 26 of the stem 16 and the axis 28 of the lug. After attachment, the fixture 60 is placed in the partially prepared canal 14 and held against the frustoconical seat S by an axial force manually applied by means of the handle 54. Thus the medical instrument 30 provides a quick and easy means for supporting the post 33 with its reference axis 36 located on the axis of the frustoconical seat S and hole H of the partially formed canal 14 that has been drilled and countersunk in the resected proximal end 12 of the femur 10. These aligned axes correspond to the axis 26 of the trochanteral portion 22 so that the tool guide 38 is set at a precise angle A for guiding a rotary cutting tool 82 for cutting a slanted groove 15 to accommodate the anti-rotation lug 24.

The medical instrument 30 is also versatile. Prosthesis stems are typically available in many sizes and shapes. Likewise, the stem 16 is available in a variety of trochanteric sizes with each respectively having three, e.g., small, medium and large, anti-rotation lug 24 sizes available to accommodate different size femurs 10. Consequently, there is a need to cut the proximal femur 10 for preparation of various lugs 24 in relationship to the frustoconical seat S. This need is met in two ways.

First, the post 33 is adjustable with respect to the collar 34 in the axial direction. Secondly, the medical instrument 30 has adjustment means for accurately locating the post 33 in a plurality of preselected axial positions relative to the collar 34.

The adjustment means for the post 33 includes an adjustment nut 67 and a bearing block 68. The adjustment nut 67 is rotatably mounted in the distal circular portion 65 of the collar 34 by bearing balls 96 that ride in ball grooves 98 of the adjustment nut 67 and matching ball grooves 100 of the collar 34, as shown in FIG. 7. The adjustment nut 67 turns in the collar 34 easily due to the bearing balls 96. The adjustment nut 67 includes a threaded bore 102 for engaging the threaded shank 46. The distal portion of the adjustment nut 67 has a knurled enlargement 103 (see FIG. 6) distally of the collar 34 that facilitates turning the adjustment nut 67 to adjust the axial position of the post 33 in the collar 34.

The bearing block 68 is disposed proximally of the adjustment nut 67 and includes a pair of ears 69, as shown in FIGS. 7 and 9. The ears 69 are disposed in the side slots of the keyway 66 and engage the flats 47 of the shank 46 for restraining the post 33 from turning in the collar 34. Thus, when the adjustment nut 67 is turned to adjust the axial position of the post 33, the post 33 is translated along the reference axis 36 without rotation.

As indicated above, the instrument 30 also includes locating means for accurately locating the adjustable post 33 in a plurality of preselected axial positions. The locating means comprises a manually operable spring-loaded detent 70 that is slideably mounted in a track 72 in the connecting side 32a of the frame 32. The track 72 intersects the collar 34 and an aligned opening in the bearing block 68 so that the shaft 73 of the detent 70 enters one of the three cross bores 48 of the post 33 upon alignment to accurately fix the post 33 in one of three preselected axial positions with respect to the collar 34, as shown in FIGS. 7 and 9. The number of bores and the length of the frame 34 can be adjusted to provide less or greater variability.

The spring-loaded detent 70 includes a T-shaped handle 74 extending laterally from the sides of the frame 32. In this manner, the detent 70 can be released manually by manipulating the T-shaped handle 74. The T-shaped handle 74 has a blind hole for receiving a spring guide pin 76 fastened in the track 72 at its opposite end by a machine screw 104, as best shown in FIGS. 7 and 9. The spring guide pin 76 guides a coil spring 78 reacting between the attached end of the pin 76 and the detent 70 to urge the shaft 73 of the detent 70 into engagement with the post 33. Thus, the distal end of the shaft 73 automatically seats in one of the cross bores 48 as the post 33 is axially adjusted.

Figure 11:
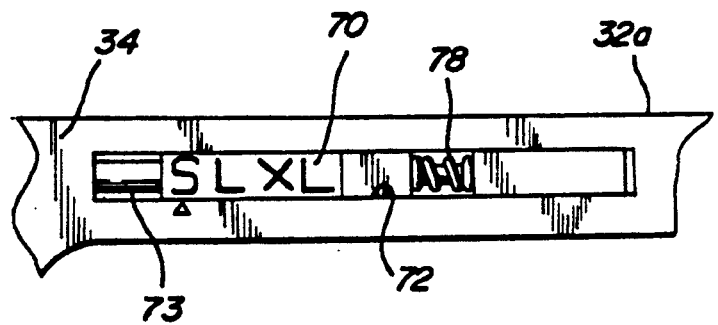
FIG. 11 is a fragmentary enlargement of the spring-loaded detent portion of the medical instrument.

Each of the three cross bores 48 is located so the detent 70 locates the post 33 and the fixture 60 precisely with respect to the collar 34 when the detent 70 enters a cross bore 48. Moreover, each of the cross bores 48 has a unique depth so that the position of handle 74 indicates which of the three bores 48 is engaged by the detent 70. Furthermore, as shown in FIG. 11, the connecting side 32a of the frame 32 and the handle 74 are provided with interacting visible indicia corresponding to the various positions of the handle 74 showing which of the three cross bores 48 is engaged by the detent 70 and, consequently, which axial adjustment of the post 33 and fixture 60 has been selected.

As indicated earlier with respect to FIG. 6, the tool guide 38 comprises spaced collars 40 for rotatably supporting a cutting tool on a precise slanted cutting axis 42. The groove 15 is cut by a rotary milling cutter 80 that has an enlarged cutting head 82 at one end of a shank 84 and an enlarged drive coupling 86 at the other end. Each collar 40 has a radial entrance slot 88 having a width matching that of two corresponding axially-spaced necks 90 cut into the shank 84, facilitating attachment of the milling cutter 80 to the instrument 30. The rotary milling cutter 80 is attached by aligning the necks 90 with the slots 88 and inserting the shank 84 laterally into the collars 40 through the slots 88. The cutter 80 is then rotated about a quarter turn and slid down the collars 40 toward the fixture 60.

The partially formed canal 14, defined by the walls of the frustoconical seat S, resulting from the basic procedures described above and shown in FIGS. 4 and 5, is finished in the following manner. The fixture 60 and milling cutter 80 are attached to the instrument 30 and the post 33 is adjusted and fixed in the appropriate position, as indicated above. The frustoconical portion 62 of the fixture 60 is then firmly engaged with the frustoconical seat S of the partially-formed canal 14 by axial pressure manually applied from the handle 54, establishing an accurate cutting axis for the rotary powered milling cutter 80. When the fixture 60 is seated, the fixture pin 63 is centered in the canal hole H to provide added stability and guaranteed coincidental axial alignment of the fixture 60 and the partially-formed canal 14. A hand-held power source connected to the end of the rotary milling cutter 80 is then operated to cut the slanted groove 15 while the instrument 30 is held down on the frustoconical seat S to maintain the accurate cutting axis during the cutting procedure. The cutting head 82 enters the bore 64 in the fixture frustoconical portion 62 during the final phase of the cutting procedure. The bore 64 is slightly larger in diameter so that the fixture 60 is not damaged. Moreover, the rotary milling cutter 80 is preferably constructed so that the drive coupling 86 bottoms on the collar 40 before the cutter head 82 bottoms in the bore 64.

The handle 54 and the drive coupling 86 are located relative to each other so that the cutting procedure of this invention can be performed by one person using one hand to hold down the instrument 30 and the other hand to operate the power source driving the rotary milling cutter 80.

The invention has been described in an illustrative manner, and it is to be understood that the terminology which has been used is intended to be in the nature of words of description rather than of limitation.

Obviously, many modifications and variations of the present invention in light of the above teachings may be made. It is, therefore, to be understood that, within the scope of the appended claims, the invention may be practiced otherwise than as specifically described.

The embodiments of the invention in which an exclusive property or privilege is claimed are defined as follows:

1. A medical instrument for preparing a proximal end of a femur to receive a prosthesis having an attached anti-rotation lug, the femur having a partially prepared canal with a countersunk frustoconical seat for receiving a trochanteral portion of the prosthesis, the instrument comprising: a frame having two spaced frame portions; a post attached to one of the frame portions and defining a reference axis; a tool guide attached to the other of the frame portions and defining a cutting axis fixed at a precise angle with respect to the reference axis; and fixture means extending from the post configured to attach to the countersunk frustoconical seat in the partially prepared canal in the femur to locate the reference axis in relation to the prepared canal so that the tool guide and the cutting axis are set at the precise angle for guiding a rotary cutting tool in the partially prepared canal to accommodate the anti-rotation lug of the prosthesis when implanted in the femur with the trochanteral portion of the prosthesis seated in the countersunk frustoconical seat.

2. An instrument as defined in claim 1 wherein the post includes a distal end, further comprising a quick-disconnect coupling disposed on the distal end of the post configured to releasibly attach the fixture means.

3. An instrument as defined in claim 1 wherein the post includes a proximal end, further comprising a handle attached to the proximal end of the post.

4. An instrument as defined in claim 2 wherein the post includes a proximal end, further comprising a coaxial handle attached to the proximal end of the post.

5. An instrument as defined in claim 1 wherein the tool guide comprises spaced collars configured to rotatably support a necked shank of a rotary cutting tool, each of the collars having an entrance slot for laterally receiving the necked shank of the rotary cutting tool.

6. An instrument as defined in claim 1 wherein the frame includes a collar surrounding a portion of the post configured to permit axial movement of the post relative to the frame.

7. An instrument as defined in claim 1 further comprising bearing block means disposed in the collar configured to prevent rotation of the post with respect to the collar.

8. An instrument as defined in claim 7 wherein the post includes an external screw thread, further comprising an adjustment nut rotatably mounted in the collar and threadably engaging the screw thread of the post for moving the post in the axial direction during rotation of the adjustment nut.

9. A medical instrument for preparing a proximal end of a femur to receive a prosthesis having attached anti-rotation lug, the femur having a partially prepared canal with a countersunk frustoconical seat for receiving a trochanteral portion of the prosthesis, the instrument comprising:
 a frame having two spaced frame portions; a post attached to one of the frame portions and defining a reference axis;
 a tool guide attached to the other of the frame portions and defining a tool axis fixed at a precise angle with respect to the reference axis;
 a rotary milling cutter operatively disposed in the tool guide configured to advancing move along the tool axis;
 a plurality of spaced collars extending from the tool guide and each of the collars having a radial entrance slot for receiving the rotary milling cutter laterally of the tool axis; and
 fixture means extending from the post configured to attach to the countersunk frustoconical seat in the partially prepared canal in the femur to locate the reference axis in relation to the prepared canal so that the tool guide and the cutting axis are set at the precise angle for guiding the cutting tool in the partially prepared canal to accommodate the anti-rotation lug of the prosthesis when implanted in the femur with the trochanteral portion of the prosthesis seated in the countersunk frustoconical seat.

10. An instrument as defined in claim 9 wherein the post includes a proximal end, further comprising a coaxial handle attached to the proximal end of the post.

11. A medical instrument for preparing a proximal end of a femur to receive a prosthesis having an attached anti-rotation lug, comprising:
 a frame having two spaced frame portions;
 a post attached to one of the frame portions and defining a reference axis; the post including an external screw thread; the post including at least one flat interrupting the screw thread;
 a tool guide attached to the other of the frame portions and defining a cutting axis fixed at a precise angle with respect to the reference axis;
 fixture means extending from the post configured to attach to a frustoconical seat in a partially prepared canal in the femur to locate the reference axis in relation to the prepared canal so that the tool guide and the cutting axis are set at the precise angle for guiding a rotary cutting tool in the partially prepared canal to accommodate the anti-rotation lug of the prosthesis when implanted in the femur;
 bearing block means disposed in the collar configured to prevent rotation of the post with respect to the collar;
 an adjustment nut rotatably mounted in the collar and threadably engaging the screw thread of the post for moving the post in the axial direction during rotation of the adjustment nut and wherein said post is disposed in sliding contact with the bearing block means.

12. A medical instrument for preparing a proximal end of a femur to receive a prosthesis having an attached anti-rotation lug, comprising:
 a frame having two spaced frame portions;
 a post attached to one of the frame portions and defining a reference axis; the post including an external screw thread;
 a tool guide attached to the other of the frame portions and defining a cutting axis fixed at a precise angle with respect to the reference axis;
 fixture means extending from the post configured to attach to a frustoconical seat in a partially prepared canal in the femur to locate the reference axis in relation to the prepared canal so that the tool guide and the cutting axis are set at the precise angle for guiding a rotary cutting tool in the partially prepared canal to accommodate the anti-rotation lug of the prosthesis when implanted in the femur;
 bearing block means disposed in the collar configured to prevent rotation of the post with respect to the collar;
 an adjustment nut rotatably mounted in the collar and threadably engaging the screw thread of the post for moving the post in the axial direction during rotation of the adjustment nut; and
 means for locating the post in a plurality of preselected axial positions with respect to the collar.

13. An instrument as defined in claim 12 wherein the means for locating the post in a plurality of preselected axial positions comprises a plurality of cross bores disposed in the post and a spring-loaded detent sequentially engageable with the cross bores.

14. An instrument as defined in claim 13 wherein each of the cross bores has a unique depth and the frame includes visible indicia showing the position of the detent.

* * * * *